(12) United States Patent
Lin

(10) Patent No.: US 10,350,378 B2
(45) Date of Patent: Jul. 16, 2019

(54) GAS GENERATOR

(71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 0 days.

(21) Appl. No.: 15/684,159

(22) Filed: Aug. 23, 2017

(65) Prior Publication Data
US 2018/0056021 A1 Mar. 1, 2018

(30) Foreign Application Priority Data

Aug. 24, 2016 (CN) .......................... 2016 1 0719446

(51) Int. Cl.
| | | |
|---|---|---|
| *C25B 15/02* | (2006.01) | |
| *C25B 1/04* | (2006.01) | |
| *C25B 9/00* | (2006.01) | |
| *A61M 16/12* | (2006.01) | |
| *A61L 9/04* | (2006.01) | |
| *A61L 9/12* | (2006.01) | |
| *C25B 1/10* | (2006.01) | |
| *C25B 9/10* | (2006.01) | |
| *C25B 15/00* | (2006.01) | |

(52) U.S. Cl.
CPC ............. *A61M 16/12* (2013.01); *A61L 9/046* (2013.01); *A61L 9/12* (2013.01); *C25B 1/10* (2013.01); *C25B 9/10* (2013.01); *C25B 15/00* (2013.01); *A61L 2209/212* (2013.01); *A61M 2202/02* (2013.01); *A61M 2202/0216* (2013.01); *Y02E 60/366* (2013.01)

(58) Field of Classification Search
CPC .. C25B 15/02; C25B 1/04; C25B 1/00; C25B 9/00; C25B 9/18; C25B 1/02; C25B 1/06; C25B 3/02
USPC .................................. 204/232; 205/752, 755
See application file for complete search history.

(56) References Cited

U.S. PATENT DOCUMENTS

| | | | |
|---|---|---|---|
| 8,945,353 B1* | 2/2015 | Fraim ................... | C02F 1/4672 204/232 |
| 2007/0272548 A1* | 11/2007 | Sutherland ................ | C25B 1/04 204/242 |
| 2014/0260208 A1* | 9/2014 | Sato ..................... | B01J 37/0246 60/286 |

FOREIGN PATENT DOCUMENTS

TW 201113224 A 4/2011

* cited by examiner

*Primary Examiner* — Zulmariam Mendez
(74) *Attorney, Agent, or Firm* — Klintworth & Rozenblat IP LLP

(57) ABSTRACT

The present invention provides a gas generator comprising an electrolytic cell, a gas pathway, and an ozonator. The electrolytic cell is configured for electrolyzing the electrolyzed water to generate the gas with hydrogen. The gas generated from the electrolytic cell is transferred by the gas pathway for human to inhale. The ozonator is connected to the gas pathway for generating ozone to enter the gas pathway. The present invention uses the ozonator to generate ozone for cleaning the gas pathway, thereby providing a pure gas with hydrogen.

19 Claims, 8 Drawing Sheets

GAS GENERATOR

CROSS-REFERENCE TO RELATED APPLICATIONS

This application claims priority to Chinese Application No. 201610719446.9, filed Aug. 24, 2016, hereby incorporated herein by reference in its entirety.

BACKGROUND OF THE INVENTION

1. Field of the Invention

The present invention relates to a gas generator, and more particularly, to a gas generator cleaning the gas pathway with ozone.

2. Description of the Prior Art

As people have always been paying much attention on health developments, many developments in medical technology are often targeted on treating diseases and prolonging human life. Also, most of the treatments in the past are passive, which means that the disease is treated only when it occurs. The treatments include an operation, a medication treatment, a radiation therapy, or a medical treatment for cancer. However, in recent years, most of the medical experts' researches are gradually moving towards preventive medical methods, such as research on healthy food, screening and the prevention of inherited diseases, and prevent diseases from occurring in the future actively. Due to the focus of the prolongation of human life, many anti-aging and anti-oxidation technologies including skin care products and anti-oxidation food/medicine are gradually being developed. Moreover, those products are becoming increasingly popular to the general public.

Studies have found that there are instable oxygen species ($O^+$), also known as free radicals, in the human body. The free radicals which are usually generated due to diseases, diet, environment and one's lifestyle can be excreted in the form of water by reacting with the inhaled hydrogen. With this method, the amount of free radicals in the human body can be reduced, thereby the body condition returns from an acidic state to an alkaline state. Also, the purpose of anti-oxidation, anti-aging and beauty health effect, and even eliminating chronic diseases can be achieved. Furthermore, there are also clinical experiments showing that patients who need to inhale a high concentration of oxygen for an extended period of time would experience lung damage. However, they could be ameliorated by inhaling hydrogen.

The gas with hydrogen for inhaling is usually generated by the electrolysis of the electrolytic water by an electrolytic device. However, the gas with hydrogen is not pure hydrogen. The gas may contain high temperature water vapor or electrolyte in the gas pathway, which breeds bacteria in the gas pathway after a period of time. Thereby, there is health concern about the use of electrolysis devices.

SUMMARY OF THE INVENTION

The present invention is to provide a gas generator for electrolyzing water to generate a gas with hydrogen and mixing the gas with hydrogen with an atomized gas to generate a healthy gas for human to inhale. At the same time, the gas generator generates ozone to clean the gas pathway to provide a pure gas with hydrogen.

The gas generator of the present invention comprises an electrolytic cell, a gas pathway, and an ozonator. The electrolytic cell accommodates the electrolyzed water comprising an electrolyte. The electrolytic cell is configured for electrolyzing the electrolyzed water to generate the gas with hydrogen. The gas pathway is connected to the electrolytic cell, for transferring the gas with hydrogen. The ozonator is configured for generating an ozone to enter the gas pathway or the electrolytic cell.

When the electrolytic cell stops electrolyzing the electrolyzed water, the ozonator generates the ozone to enter the gas pathway or the electrolytic cell.

The gas generator further comprises an ozone pump connected to the gas pathway, wherein the ozone pump provides a negative pressure to inhale the ozone to the gas pathway.

The gas generator further comprises an atomization device connected to the gas pathway for generating an atomized gas and receiving the gas with hydrogen to mix the atomized gas with the gas with hydrogen to generate a healthy gas.

The gas generator further comprises a condensing filter, a wetting cup, and a replenishing cup; the condensing filter is connected to the electrolytic cell for receiving, condensing, and filtering the gas with hydrogen; the wetting cup is connected to the condensing filter for receiving and wetting the gas with hydrogen; and the replenishing cup is connected between the wetting cup and the atomization device for replenishing water.

The gas pathway is connected to the electrolytic cell, the condensing filter, the wetting cup, the replenishing cup and the atomization device for transferring the gas with hydrogen. Wherein, the ozonator is connected to the gas pathway between the condensing filter and wetting cup.

The atomization device comprises an atomizing chamber and a mixing reaction chamber. The atomizing chamber is configured for generating the atomized gas, and the mixing reaction chamber is connected to the gas pathway for receiving the gas with hydrogen to mix the atomized gas with the gas with hydrogen to generate the healthy gas.

To summarize, the object of the present invention is to provide a gas generator comprising an electrolytic cell, a gas pathway and an ozonator. In the gas generator of the present invention, the gas with hydrogen generated by the electrolytic cell is transferred by the gas pathway for human to inhale. The ozonator is connected to the gas pathway for generating the ozone to clean the gas pathway to provide a pure gas with hydrogen.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1A:
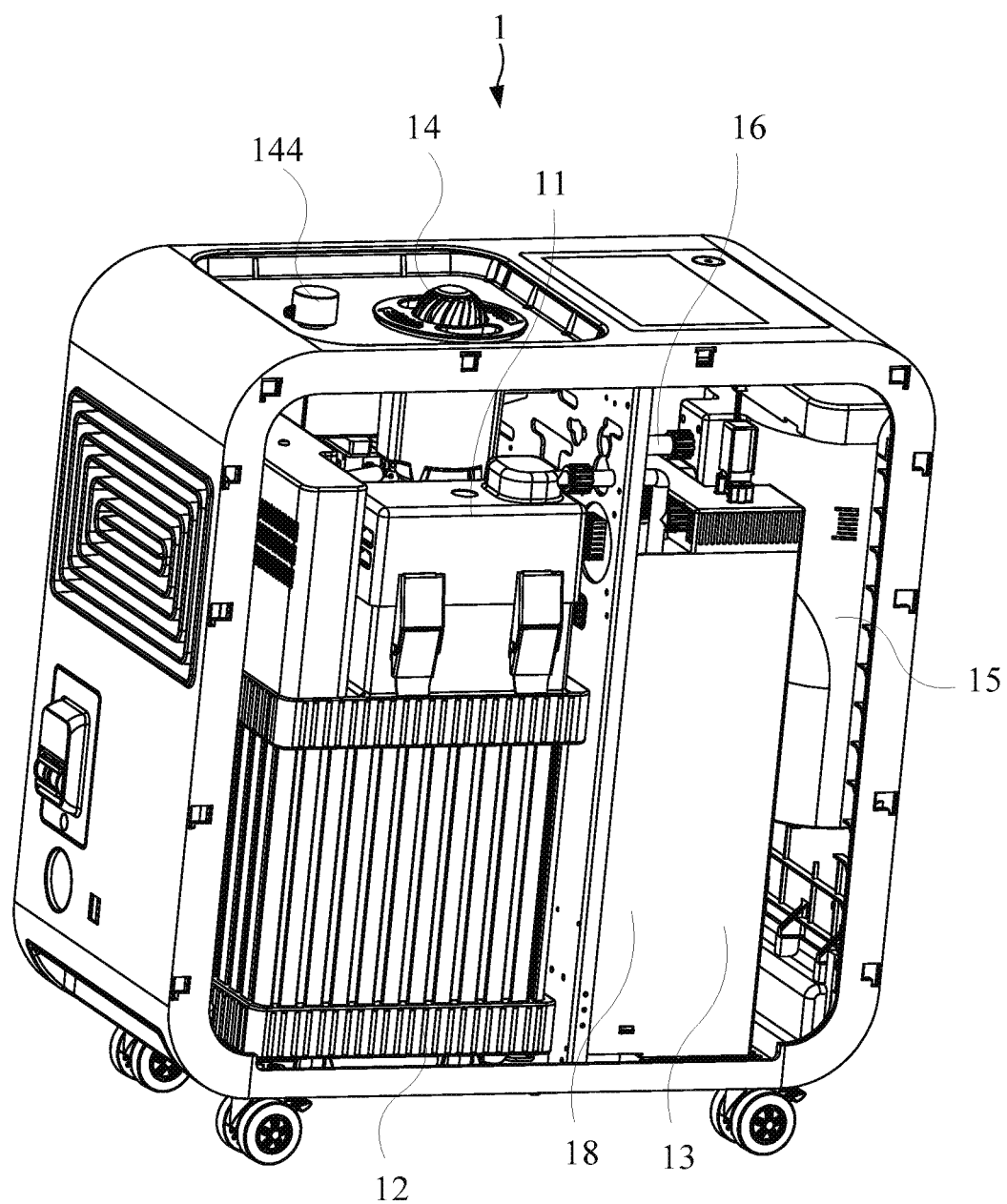
FIG. 1A and FIG. 1B show a schematic diagram of the gas generator in an embodiment with different visual angles of the present invention.
Figure 1B:
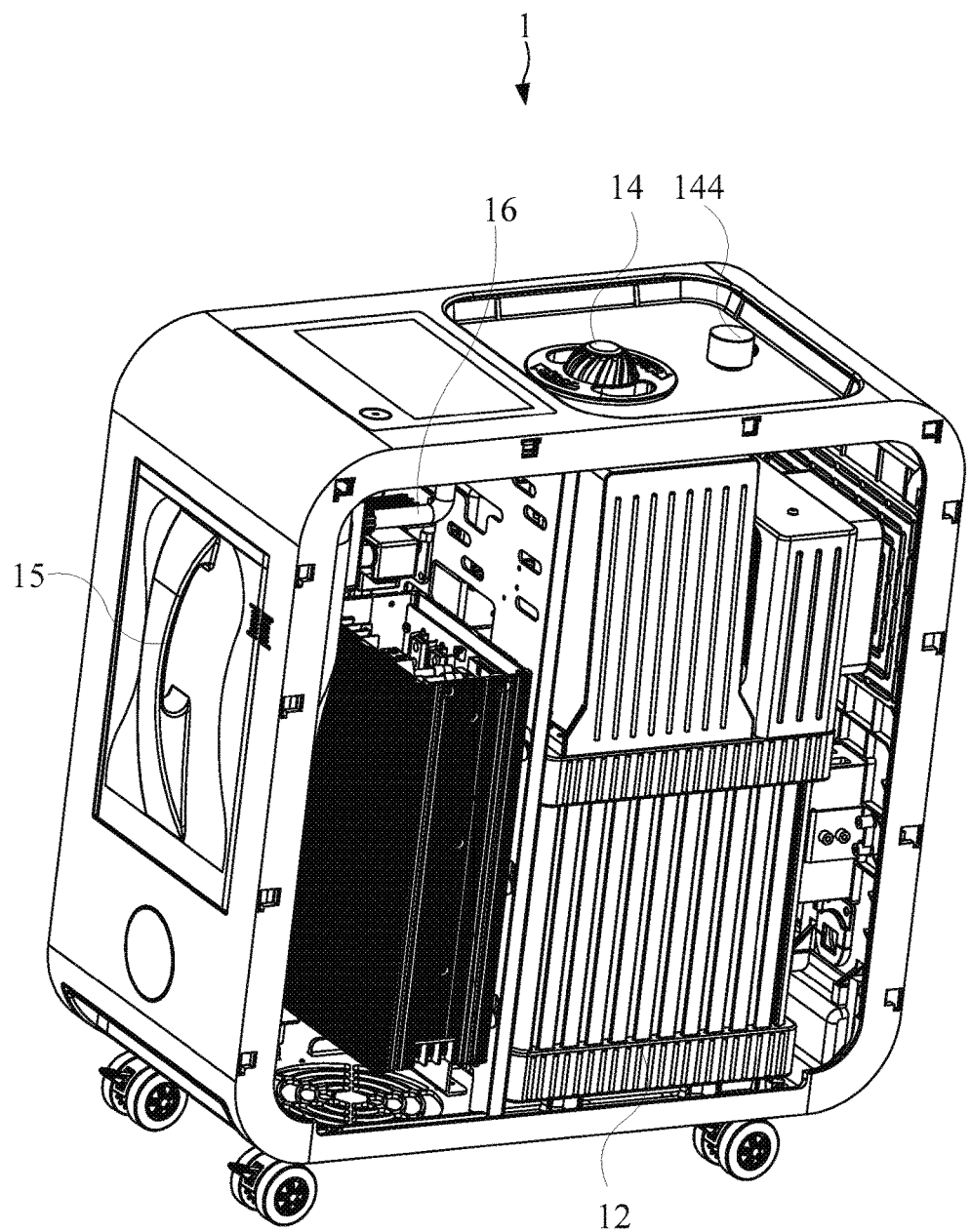
Figure 2A:
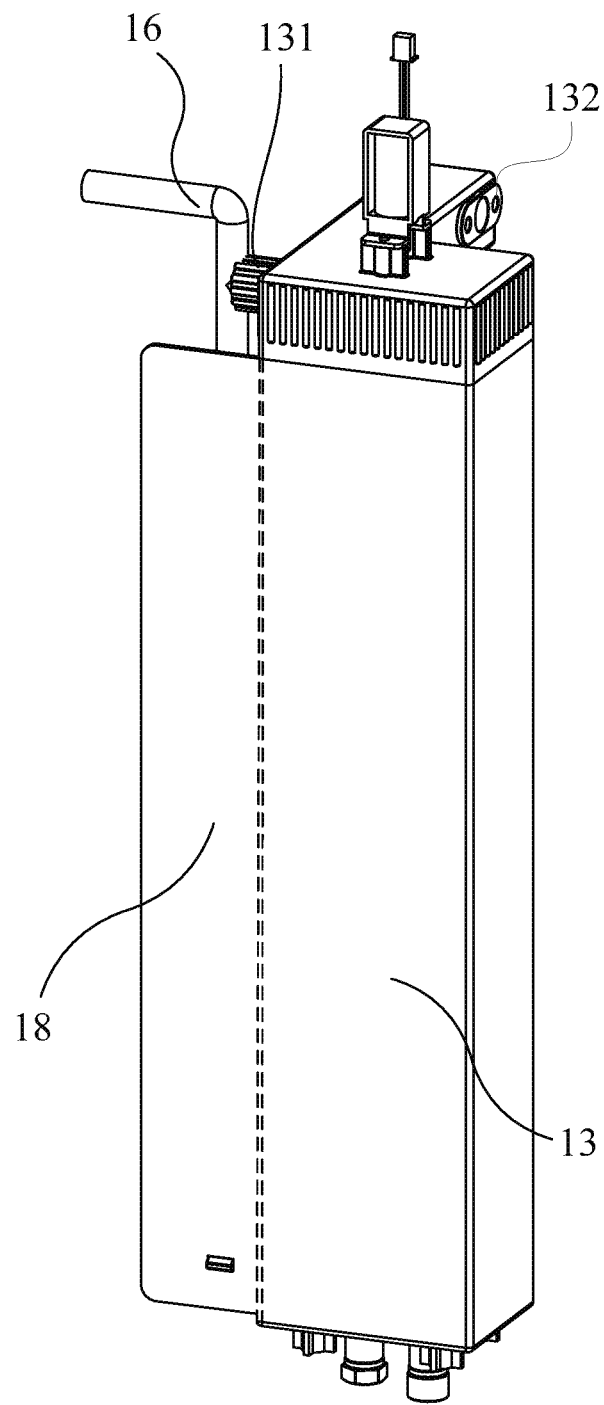
FIG. 2A and FIG. 2B show a schematic diagram of the ozonator in the gas generator in an embodiment with different visual angles of the present invention.
Figure 2B:
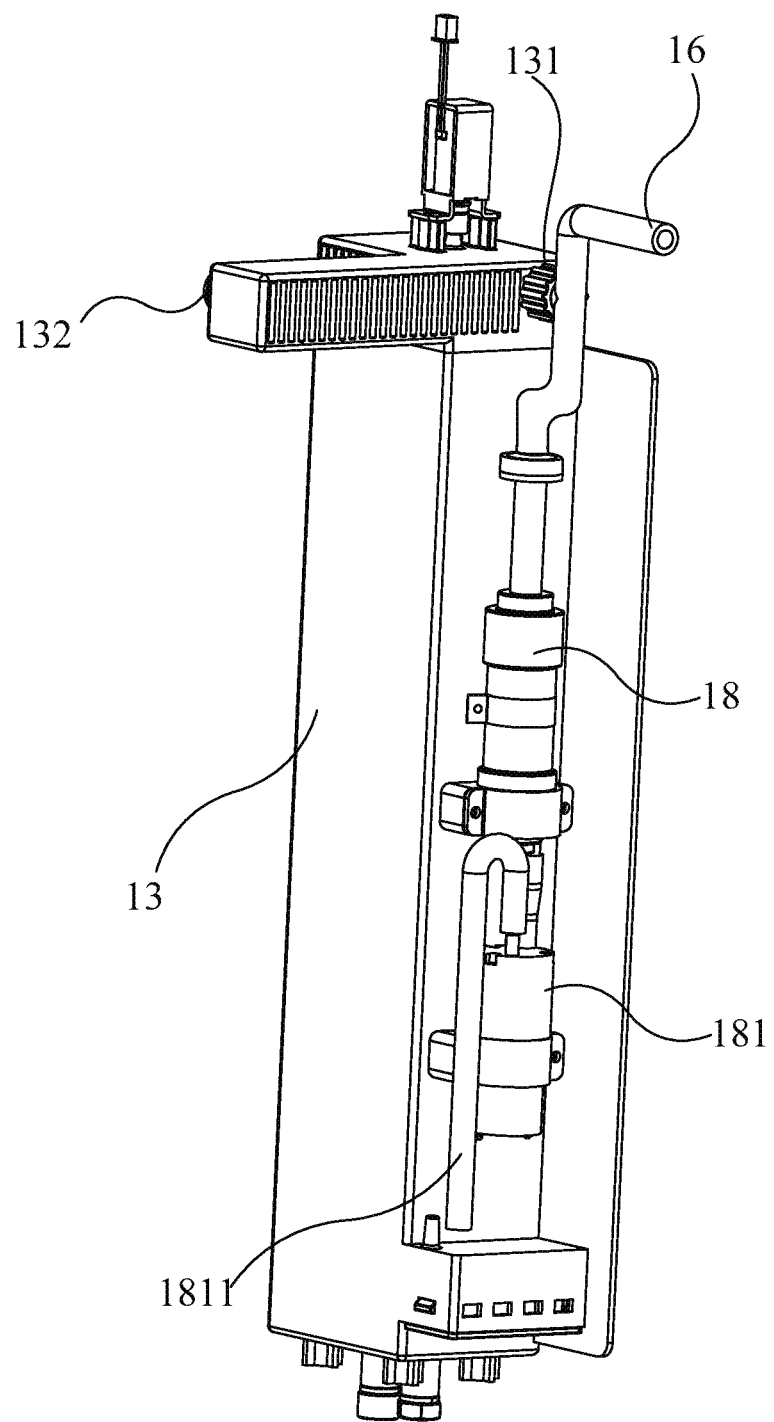

Please refer to FIG. 1A, FIG. 1B, FIG. 2A, and FIG. 2B. FIG. 1A and FIG. 1B show a schematic diagram of the gas generator 1 in an embodiment with different visual angles of the present invention. FIG. 2A and FIG. 2B show a schematic diagram of the ozonator 18 in the gas generator 1 in an embodiment with different visual angles of the present invention. The gas generator 1 of the present invention comprises an electrolytic cell 12, a gas pathway 16, and an ozonator 18. The electrolytic cell 12 accommodates the electrolyzed water comprising an electrolyte. The electrolytic cell 12 is configured for electrolyzing the electrolyzed water to generate the gas with hydrogen. The gas pathway 16 is connected to the electrolytic cell 12, for transferring the gas with hydrogen. The ozonator 18 is configured for generating an ozone to enter the gas pathway 16 or the electrolytic cell 12.

The gas generator 1 comprises an atomization device 14 connected to the gas pathway 16 for generating an atomized gas and receiving the gas with hydrogen to mix the atomized gas with the gas with hydrogen to generate a healthy gas.

Figure 6:
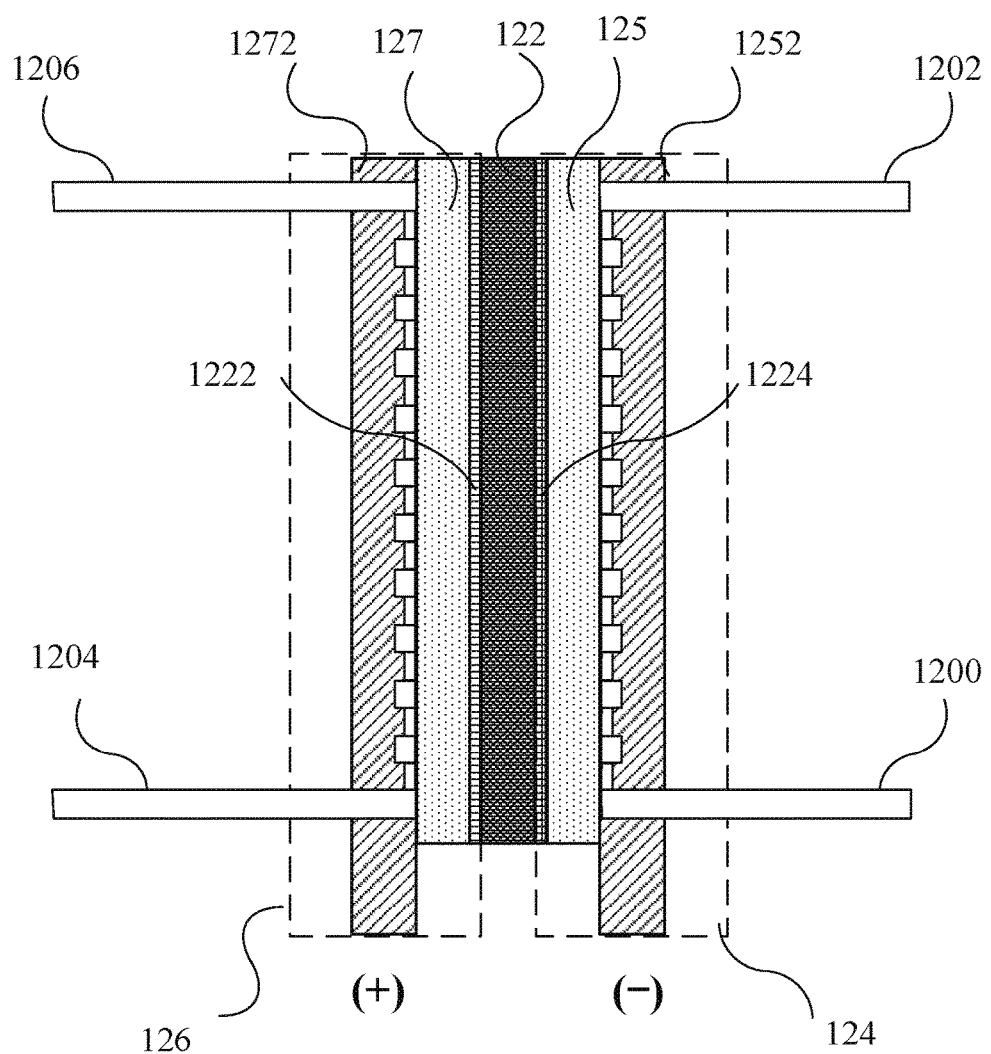
FIG. 6 illustrates a schematic diagram of the ion membrane electrolytic cell of the gas generator in an embodiment of the present invention.

Please refer to FIG. 6. FIG. 6 illustrates a schematic diagram of the ion membrane electrolytic cell of the gas generator 1 in an embodiment of the present invention. In an embodiment, the electrolytic cell 12 comprises an ion membrane electrolytic device, and the ion membrane electrolytic device comprises an ion exchange membrane 122, a cathode chamber 124 and an anode chamber 126. The cathode electrode 125 is set in the cathode chamber 124. The anode electrode 127 is set in the anode chamber 126. The ion exchange membrane 122 is set between the anode chamber 126 and the cathode chamber 124 (for the sake of clarity, the anode chamber 126 and the cathode chamber 124 are indicated by a dotted line). Oxygen is generated by the anode electrode 127 and hydrogen is generated by the cathode electrode 125 while the ion membrane electrolytic device electrolyzes water. In an embodiment, water is contained in the anode chamber 126, and water in the anode chamber 126 may, but not limited to, further penetrate into the cathode chamber 124 through the ion exchange membrane 122. In another embodiment, the anode chamber 126 and the cathode chamber 124 can accommodate water at the same time. The anode electrode 127 can electrolyze water to generate hydrogen ion and oxygen. The hydrogen ion can penetrate through the ion exchange membrane 122 to the cathode chamber 124, and hydrogen is generated on the cathode electrode 125 after getting the electrode. In practice, hydrogen can be generated, but not limited to, on the catalyst layer; hydrogen can also be generated on the electrode plate or between the ion membrane and the electrode plate.

Besides, the ion membrane electrolytic device comprises a cathode current-conducting plate 1252 and an anode current-conducting plate 1272. The anode electrode 127 or the cathode electrode 125 of the ion membrane electrolytic device can be connected with an external power source by the cathode current-conducting plate 1252 and the anode current-conducting plate 1272. Furthermore, the ion membrane electrolytic device can further comprise a gas tube 1200, and the gas tube 1200 can connect the cathode chamber 124 and the outside. The ion membrane electrolytic device can further comprise the hydrogen tube 1202 connected to the cathode chamber 124 to transfer the gas with hydrogen into the gas pathway 16. The ion membrane electrolytic device can further comprise a water supply tube 104 to recharge water from the electrolytic cell 12 into the cathode chamber 124 and the anode chamber 126. The ion membrane electrolytic device can further comprise an oxygen tube 1206 connected with the anode chamber 126 to output oxygen to the outside from the electrolytic cell 12. Besides, the ion membrane electrolytic cell 12 can further comprise a ratio regulator (not shown) connected to the hydrogen tube 1202 and the gas pathway 16, and is further connected to the gas tube 1200 or the oxygen tube 1206. Therefore, the hydrogen concentration is regulated to generate the gas with hydrogen as-needed and then the gas with hydrogen is transferred to the gas pathway 16.

In practical application, the ion exchange membrane 122 further comprises an anode catalyst layer 1222 and a cathode catalyst layer 1224. The anode catalyst layer 1222 can be selected from a group consisting of Pt, Ir, Pd, the alloy powder of Pt, carbon or any combination thereof. The cathode catalyst layer 1224 can be selected from a group consisting of Pt, Ir, Pd, the alloy powder of Pt, or any combination thereof. In an embodiment, the material of the anode catalyst layer 1222 or the cathode catalyst layer 1224 can be configured into slurry to be coated on both sides of the ion membrane to form the anode catalyst layer 1222 and the cathode catalyst layer 1224.

Figure 5:
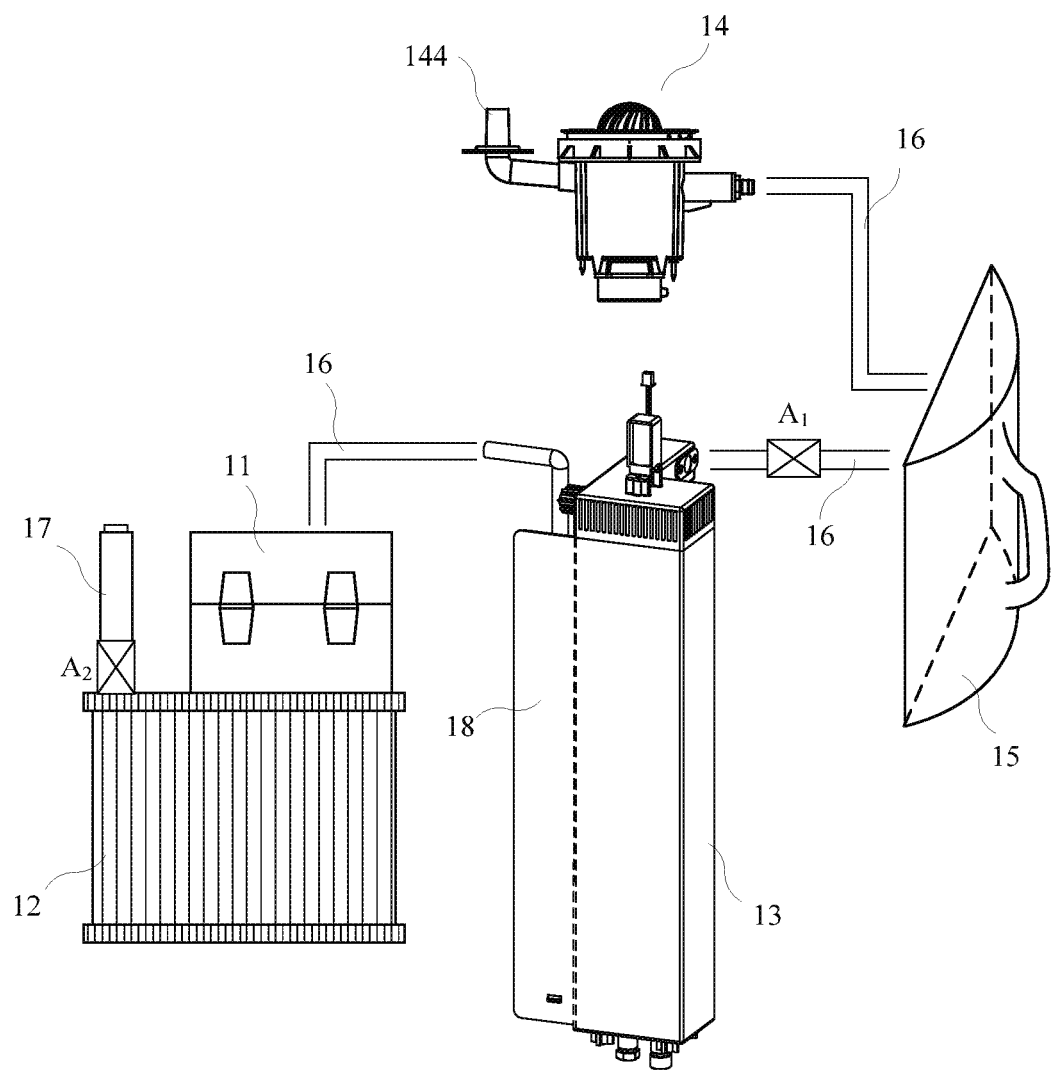
FIG. 5 illustrates a schematic diagram of the ozone cleaning pathway of the gas generator in an embodiment of the present invention.

Please refer to FIG. 5. FIG. 5 illustrates a schematic diagram of ozone cleaning pathway of the gas generator 1 in an embodiment of the present invention. When the electrolytic cell 12 stops electrolyzing the electrolyzed water, the ozonator 18 generates the ozone to enter the gas pathway 16 or the electrolytic cell 12.

The gas generator 1 further comprises an electrolytic pump 17 (not shown) connected to the electrolytic cell 12, and the electrolytic pump 17 provides a negative pressure to inhale the ozone to the electrolytic cell 12.

The gas generator 1 further comprises a condensing filter 11, a wetting cup 13, and a replenishing cup 15; the condensing filter 11 is connected to the electrolytic cell 12 for receiving, condensing and filtering the gas with hydrogen; the wetting cup 13 is connected to the condensing filter 11 for receiving and wetting the gas with hydrogen; and the replenishing cup 15 is connected between the wetting cup 13 and the atomization device 14 for replenishing water.

The gas pathway 16 is connected to the electrolytic cell 12, the condensing filter 11, the wetting cup 13, the replenishing cup 15 and the atomization device 14 for transferring the gas with hydrogen, wherein the ozonator 18 is connected to the gas pathway 16 between the condensing filter 11 and wetting cup 13.

In practice, the water of the replenishing cup 15 can be configured to replenish the wetting liquid of the wetting cup 13, or the water in the replenishing cup 15 can be drawn through the electrolytic pump 17 of the electrolytic cell 12 to the electrolytic cell 12 for being electrolyzed into the gas with hydrogen. At the same time, the water in the replenishing cup 15 flows through the wetting cup 13, the condensing filter 11 and the electrolytic cell 12 in order. The gas pathway 16 between the electrolytic cell 12 and the replenishing cup 15 can be washed with clear water reversely. Moreover, the volatile electrolyte can be rinsed back to the electrolytic water of the electrolytic cell 12, in order to let the electrolyte re-use and reduce the consumption of electrolytes. Therefore, the gas pathway 16 and the flow-through device are not blocked by the crystallization of the electrolyte.

Please refer to FIG. 2B and FIG. 5. The ozone generated by the ozonator 18 and the gas with hydrogen generated by the electrolytic cell 12 are transferred to a wetting cup inlet 131 through the gas pathway 16 to enter the wetting cup 13 and then transferred out of the wetting cup 13 through a wetting cup outlet 132.

The gas generator 1 further comprises an ozone pump 181 connected to the gas pathway 16, wherein the ozone pump 181 provides a negative pressure to inhale the ozone to the gas pathway 16.

It should be noted that the term "connected" herein merely represents a direct or indirect connection and also means that the ozonator 18 can be placed in a place of the gas generator. The gas with hydrogen exists in the place of the gas generator or the healthy gas passes through the place of the gas generator. Therefore, the place of the gas generator can be the electrolytic cell 12, the atomization device 14, the gas pathway 16, or the outlet for inhaling the healthy gas.

In practice, the ozone pump 181 further comprises an ozone pump exhaust pipe 1811 for exhausting the gas in the gas pathway 16.

The gas pathway 16 can further comprise a flow valve for sealing the gas pathway 16. In practice, the flow valve can block the communication port between the gas pathway 16 and the outside when the electrolytic cell 12 stops electrolyzing electrolyzed water. Then the ozone pump 181 is activated to cause the pressure in the gas pathway 16 to become negative pressure (lower than the original pressure or external environmental pressure). After a reaction time through the ozone sterilization, open the flow valve to exhaust the ozone within the gas pathway 16.

In practice, the flow valve may also be a plurality of airtight valves making the gas pathway 16 sealed in sections. The gas pathway 16 can go through leak detection in sections via the negative pressure generated by connecting the electrolytic pump 17 or the ozone pump 181 of the electrolytic cell 12 with the gas pathway 16 and the ozone or the gas to hydrogen generated by the gas generator 1.

The gas generator 1 further comprises a first directional switch A1. The gas generator 1 selectively opens the first direction switch A1 and the ozone pump 181 so that the ozone enters the gas pathway 16. Besides, the gas generator 1 further comprises a second directional switch A2; the gas generator 1 selectively opens the second direction switch A2 and the ozone electrolytic pump 17 so that the ozone enters the electrolytic cell 12. In addition, the gas generator 1 can comprise a bidirectional switch (not shown); the gas generator 1 selectively adjusts the bidirectional switch so that the ozonator 18 is connected to the gas pathway 16 or the electrolytic cell 12.

The gas generator 1 generates ozone to enter the gas pathway 16 or the electrolytic cell 12 for a sterilization time. Then the gas generator 1 closes the ozonator 18 and then electrolyzes the electrolyzed water to reduce or eliminate ozone in the gas generator 1.

In an embodiment without the second direction switch A2 and the electrolytic pump 17, the steps of the ozone cleaning gas generator 1 can be as followings: The first direction switch A1 is turned off and the ozone pump 181 is turned on so that the ozone pump 181 can exhaust the gas in space of the ozonator 18 to the opposite direction of the first direction switch A1. Next, after the ozone pump 181 is turned off and ozone is generated, the ozone fills the entire space. The above actions can be repeated several times to clean the space with ozone. Then, the first direction switch A1 is turned on, and the ozone is intended to escape from the healthy gas outlet 144 with lower pressure for the purpose of ozone sterilization due to the perfusion of the ozone in the entire gas generator 1. After that, the ozonator 18 is turned off and the electrolytic cell 12 electrolyzes electrolyzed water to generate the gas with hydrogen to remove ozone in the gas generator 1.

In another embodiment without the first direction switch A1 and the ozone pump 181, the steps of the ozone cleaning gas generator 1 can be as followings: The electrolytic pump 17 is turned off and the second direction switch A2 is turned on so that the pressure in the electrolytic cell 12 is less than the original pressure. Next, the residual gas between the ozonator 18 and the electrolytic cell 12 is exhausted through the electrolytic pump 17. The ozonator 18 is turned on so that the ozone can be filled in the space between the ozonator 18 and the electrolytic cell 12 with lower pressure. After a period of time, the electrolytic pump 17 and the second direction switch A2 are turned off. Meanwhile, the ozone is continuously generated, and then the ozone is allowed to escape from the only opening healthy gas outlet 144, so that the ozone can be filled in the entire gas generator 1 space for the purpose of ozone sterilization. After that, the ozonator 18 is turned off and the electrolytic cell 12 electrolyzes electrolyzed water to generate the gas with hydrogen again to remove ozone in the gas generator 1.

In an embodiment, the steps of the ozone cleaning gas generator 1 can be as followings: The ozone pump 181 is turned on and the first direction switch A1 is turned off. Then, the second direction switch A2 is turned on to cause a negative pressure within the electrolytic cell 12, the condensation filter 11, the ozone pump 181 and the gas pathway 16 for the ozone to enter; at the same time, the electrolytic pump 17 can be turned on. After a predetermined time, for example, ten seconds later, the ozone generator 18 is turned on to generate ozone, and the ozone flows through the gas pathway 16 to the condensation filter 11 and the electrolytic cell 12; meanwhile, the ozone can be extracted out through the electrolysis pump 17, or flow to the electrolysis pump 17 by turning off the pump 181. After a sterilization time, for example, three minutes later, turn off the ozone pump 181, the electrolyze pump 17 and the second direction switch A2, and simultaneously turn on the first direction switch A1. Since the ozonator 18 continues to generate ozone, the pressure of the electrolytic cell 12 is higher than the pressure of the replenishing cup 15 after a period of time, whereby the ozone is sequentially passed through the wetting cup 13, the replenishing cup 15, the atomization device 14, and the gas pathway 16, and the ozone is exhausted through the healthy gas outlet 144. After five minutes, the ozonator 18 is turned off and the electrolytic cell 12 electrolyzes the water again to generate the gas with hydrogen. Then the residual ozone is exhausted by the healthy gas outlet 144. After ten minutes, stop electrolyzing water to complete the ozone cleaning process.

In an embodiment, there is a bidirectional switch (not shown) that can be configured to determine the ozone flows to the electrolytic cell 12 or the healthy gas outlet 144 by operating the bidirectional switch to achieve a more selective cleaning purpose.

Figure 3:
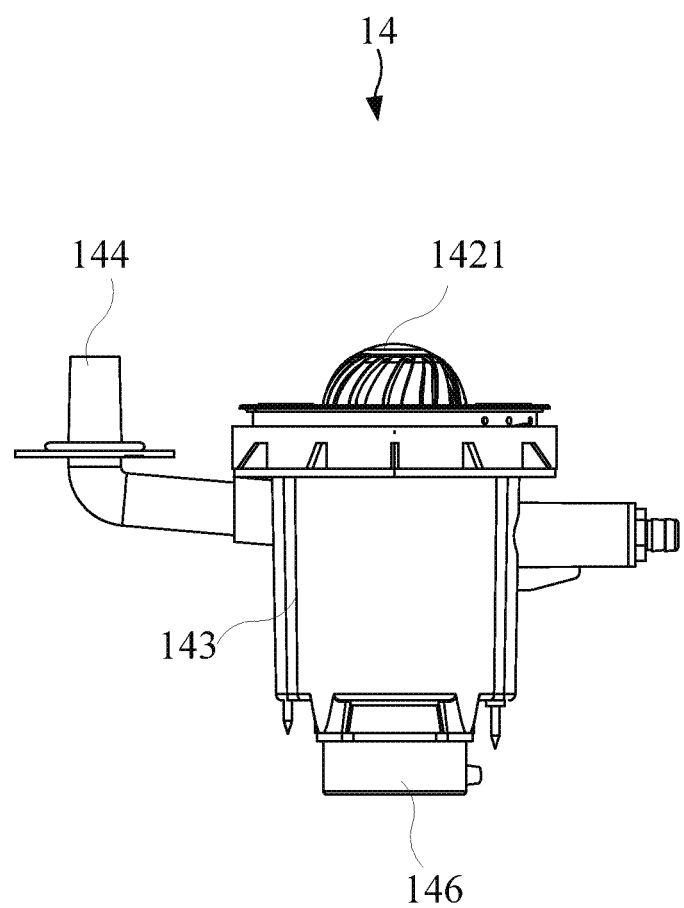
FIG. 3 illustrates a schematic diagram of the atomization device of the gas generator in an embodiment of the present invention.
Figure 4:
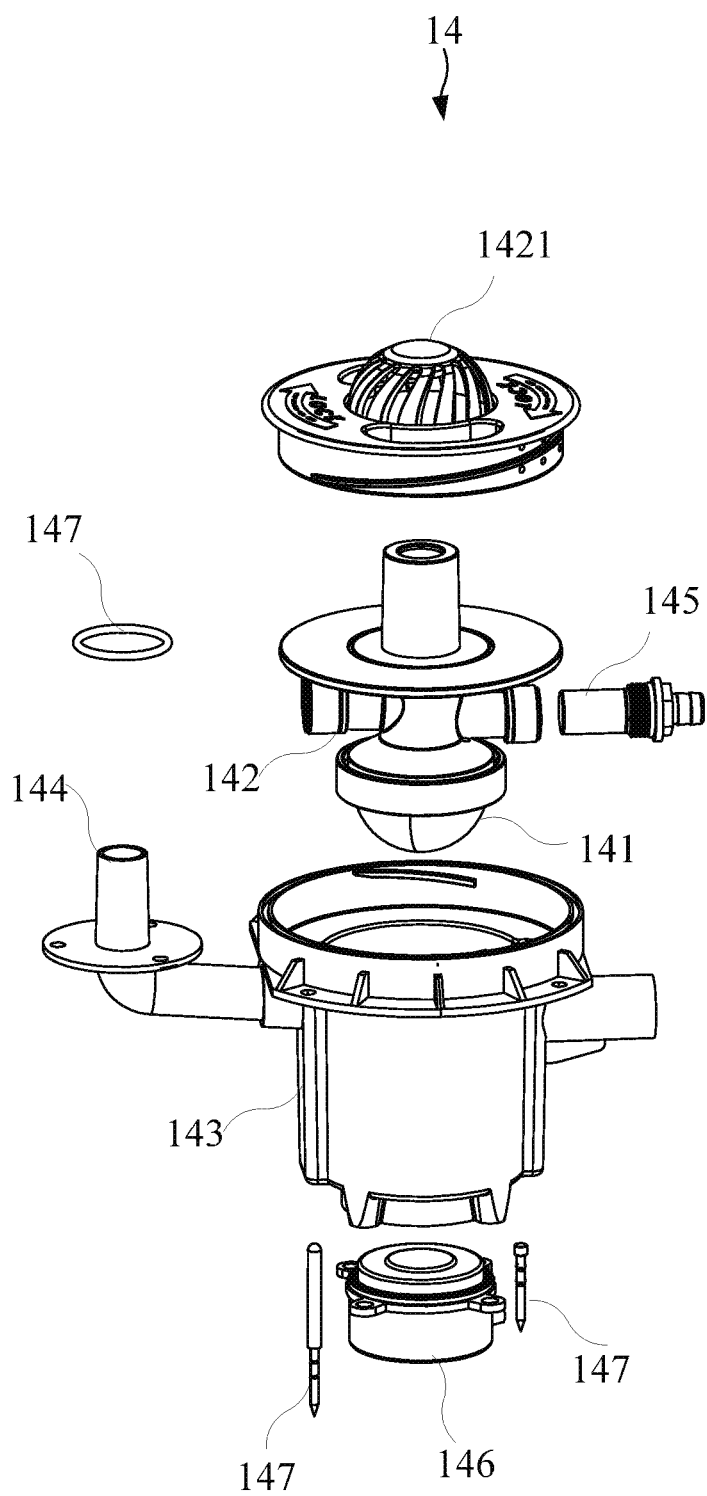
FIG. 4 illustrates an explosion diagram of the atomization device of the gas generator in an embodiment of the present invention.

Please refer to FIG. 3 and FIG. 4. FIG. 3 illustrates a schematic diagram of the atomization device 14 of the gas generator 1 in an embodiment of the present invention. FIG. 4 illustrates an explosion diagram of the atomization device 14 of the gas generator 1 in an embodiment of the present invention. The atomization device 14 comprises an atomizing chamber 141 and a mixing reaction chamber 142; the atomizing chamber 141 is configured for generating the atomized gas. The mixing reaction chamber 142 is connected to the gas pathway 16 and the atomizing chamber 141, respectively, for receiving the gas with hydrogen to mix the atomized gas with the gas with hydrogen to generate the healthy gas. The atomized gas is selected from one of the groups consisting of water vapor, atomized solution, volatile essential oil and combinations thereof.

In practical application, the atomization device 14 can further comprise a shaker 146. The atomizing chamber 141 carries the required atomized gas precursor. The shaker 146 is configured for oscillating the atomized gas precursor in the atomizing chamber 141 into the atomized gas as-needed.

In practice, the atomization device 14 can further comprise a gas communication tube 145 for connecting the mixing reaction chamber 142 and the gas pathway 16. In addition, the atomization device 14 comprises a healthy gas outlet 144 for the user to breathe in the healthy gas. Besides, the atomization device 14 can further comprise an atomization device shell 143 for fixing the position of the other parts of the atomization device 14.

Furthermore, the atomization device 14 can comprise an anti-static element 147 set at a position in contact with the gas with hydrogen or the healthy gas. The anti-static element 147 can be a conductor. The anti-static element 147 contacts with the atomization device shell 143 and then the atomization device shell 143 is grounded. Therefore, the potential of the gas with hydrogen or the healthy gas and the environment make a potential balance, so that the charge will not be accumulated to produce static electricity, even the risk of gas explosion caused by the static electricity will not be generated.

In practice, the mixing reaction chamber 142 additionally comprises an explosion-proof hole 1421 for preventing the gas with hydrogen from exploding in the gas pathway 16. The explosion-proof hole 1421 can be composed of a silicone. When the gas generator 1 occurs the gas with hydrogen or the healthy gas explosion, the gas can be released through the most fragile explosion-proof hole 1421. Therefore, the other devices within the gas generator 1 and the gas pathway 16 are protected from the possibility of the device damage or person injury even.

In addition, the atomization device 14 can comprise a gas flow valve for regulating the amount of the exhausted healthy gas so that the user can adjust the intake amount.

To summarize, the objective of the present invention is to provide a gas generator comprising an electrolytic cell, a gas pathway and an ozonator. In the gas generator of the present invention, the gas with hydrogen generated by the electrolytic cell is transferred by the gas pathway for human to inhale. The ozonator is connected to the gas pathway for generating the ozone to clean the gas pathway, so that a pure gas with hydrogen can be provided.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator, comprising:
    an electrolytic cell, accommodating an electrolyzed water comprising an electrolyte, for electrolyzing the electrolyzed water to generate a gas with hydrogen;
    a gas pathway, connected to the electrolytic cell, for transferring the gas with hydrogen; and
    an ozonator, for generating an ozone to enter the gas pathway or the electrolytic cell when the electrolytic cell stops electrolyzing the electrolyzed water.

2. The gas generator of claim 1, further comprising an ozone pump connected to the gas pathway, wherein the ozone pump provides a negative pressure to inhale the ozone to the gas pathway.

3. The gas generator of claim 2, wherein the gas generator further comprises a first direction switch, and the gas generator selectively opens the first direction switch and the ozone pump so that the ozone enters the gas pathway.

4. The gas generator of claim 1, wherein the gas generator further comprises an electrolytic pump connected to the electrolytic cell, and the electrolytic pump provides a negative pressure to inhale the ozone to the electrolytic cell.

5. The gas generator of claim 4, wherein the gas generator further comprises a second direction switch, and the gas generator selectively opens the second direction switch and the electrolytic pump so that the ozone enters the electrolytic cell.

6. The gas generator of claim 1, further comprising a bidirectional switch, wherein the gas generator selectively adjusts the bidirectional switch so that the ozonator is connected to the gas pathway or the electrolytic cell.

7. The gas generator of claim 1, wherein the gas generator generates the ozone to enter the gas pathway or the electrolytic cell for a sterilization time, and the gas generator closes the ozonator and electrolyzes the electrolyzed water to reduce or eliminate the ozone in the gas generator.

8. The gas generator of claim 1, wherein the gas generator further comprises an atomization device connected to the gas pathway for generating an atomized gas and receiving the gas with hydrogen to mix the atomized gas with the gas with hydrogen to generate a healthy gas.

9. The gas generator of claim 8, wherein the gas generator further comprises a condensing filter, a wetting cup, and a replenishing cup; the condensing filter is connected to the electrolytic cell for receiving and condensing and filtering the gas with hydrogen, and the wetting cup is connected to the condensing filter for receiving and wetting the gas with hydrogen, and the replenishing cup is connected between the wetting cup and the atomization device for replenishing water.

10. The gas generator of claim 9, wherein the gas pathway is connected to the electrolytic cell, the condensing filter, the wetting cup, the replenishing cup and the atomization device for transferring the gas with hydrogen.

11. The gas generator of claim 10, wherein the ozonator is connected to the gas pathway between the condensing filter and wetting cup.

12. A gas generator, comprising:
an electrolytic cell configured to electrolyze an electrolyzed water to generate a gas with hydrogen;
a gas pathway configured to transfer the gas with hydrogen; and
an ozonator coupled to gas pathway and capable to generate an ozone to the gas pathway when the electrolytic cell stops electrolyzing the electrolyzed water.

13. The gas generator of claim 12, further comprising a switch set connected to the gas pathway to control the ozone to flow to the electrolytic cell or to a healthy gas outlet in the gas pathway.

14. The gas generator of claim 13, wherein the switch set further comprises a first direction switch configured between the ozonator and the healthy gas outlet, and the gas generator selectively opens the first direction switch to control the ozone to flow to the healthy gas outlet.

15. The gas generator of claim 13, wherein the switch set further comprises a second direction switch configured on the electrolytic cell, and the gas generator selectively opens the second direction switch to control the ozone to flow to the electrolytic cell.

16. The gas generator of claim 13, wherein the switch set further comprises a bidirectional switch, and the gas generator selectively adjusts the bidirectional switch so that the ozonator is connected to the gas pathway or the electrolytic cell.

17. The gas generator of claim 12, wherein the gas generator generates the ozone to enter the gas pathway or the electrolytic cell for a sterilization time, and the gas generator closes the ozonator and electrolyzes the electrolyzed water to reduce or eliminate the ozone in the gas generator.

18. The gas generator of claim 12, wherein the gas generator generates the ozone to enter the gas pathway or the electrolytic cell for a sterilization time, and the gas generator closes the ozonator and electrolyzes the electrolyzed water to reduce or eliminate the ozone in the gas generator.

19. The gas generator of claim 12, wherein the gas generator further comprises an atomization device connected to the gas pathway for generating an atomized gas and receiving the gas with hydrogen to mix the atomized gas with the gas with hydrogen to generate a healthy gas.

* * * * *